(12) United States Patent
Clough

(10) Patent No.: US 11,051,933 B2
(45) Date of Patent: *Jul. 6, 2021

(54) ASPHERICAL MULTIFOCAL INTRAOCULAR LENS

(71) Applicant: Lenstec Barbados Inc.

(72) Inventor: John Clough, St. Pete Beach, FL (US)

(73) Assignee: Lenstec Barbados Inc.

( * ) Notice: Subject to any disclaimer, the term of this patent is extended or adjusted under 35 U.S.C. 154(b) by 33 days.

This patent is subject to a terminal disclaimer.

(21) Appl. No.: 16/421,947

(22) Filed: May 24, 2019

(65) Prior Publication Data

US 2019/0274821 A1 Sep. 12, 2019

Related U.S. Application Data

(63) Continuation of application No. 15/855,658, filed on Dec. 27, 2017, now Pat. No. 10,299,911, which is a continuation of application No. 15/209,313, filed on Jul. 13, 2016, now Pat. No. 9,889,001, which is a continuation of application No. 13/671,900, filed on Aug. 11, 2012, now Pat. No. 9,433,496.

(51) Int. Cl.
*A61F 2/16* (2006.01)

(52) U.S. Cl.
CPC ............. *A61F 2/1618* (2013.01); *A61F 2/16* (2013.01); *A61F 2/164* (2015.04); *A61F 2/1613* (2013.01); *A61F 2/1648* (2013.01); *A61F 2/1637* (2013.01); *A61F 2002/1689* (2013.01); *A61F 2250/0053* (2013.01)

(58) Field of Classification Search
CPC ........ A61F 2/16; A61F 2/1613; A61F 2/1618; A61F 2/164; A61F 2/1637; A61F 2/1648
See application file for complete search history.

(56) References Cited

U.S. PATENT DOCUMENTS

| | | | |
|---|---|---|---|
| 5,236,452 A | 8/1993 | Nordan | |
| 5,245,366 A | 9/1993 | Svochak | |
| 5,507,806 A | 4/1996 | Blake | |
| 5,800,532 A | 9/1998 | Leiberman | |
| 6,261,321 B1 | 7/2001 | Kellan | |
| 6,409,339 B1 | 6/2002 | Wanders | |
| 7,281,795 B2 | 10/2007 | Sandstedt et al. | |
| 7,350,918 B2 | 4/2008 | Clough et al. | |
| 9,433,496 B2 * | 9/2016 | Clough | A61F 2/164 |
| 9,889,001 B2 * | 2/2018 | Clough | A61F 2/1618 |

(Continued)

FOREIGN PATENT DOCUMENTS

| EP | 2111822 | 10/2009 |
|---|---|---|
| EP | 2219065 | 1/2012 |

(Continued)

OTHER PUBLICATIONS

Extended European Search Report for Application No. 13185822.7 dated Feb. 7, 2014.

(Continued)

*Primary Examiner* — William H Matthews
(74) *Attorney, Agent, or Firm* — Tumey L.L.P.

(57) ABSTRACT

A multifocal intraocular lens has an anterior lens surface which includes a first optic of a first radius and a second optic of a different radius. The posterior surface of the lens include an aspheric surface.

8 Claims, 2 Drawing Sheets

(56) References Cited

U.S. PATENT DOCUMENTS

Figure 1:
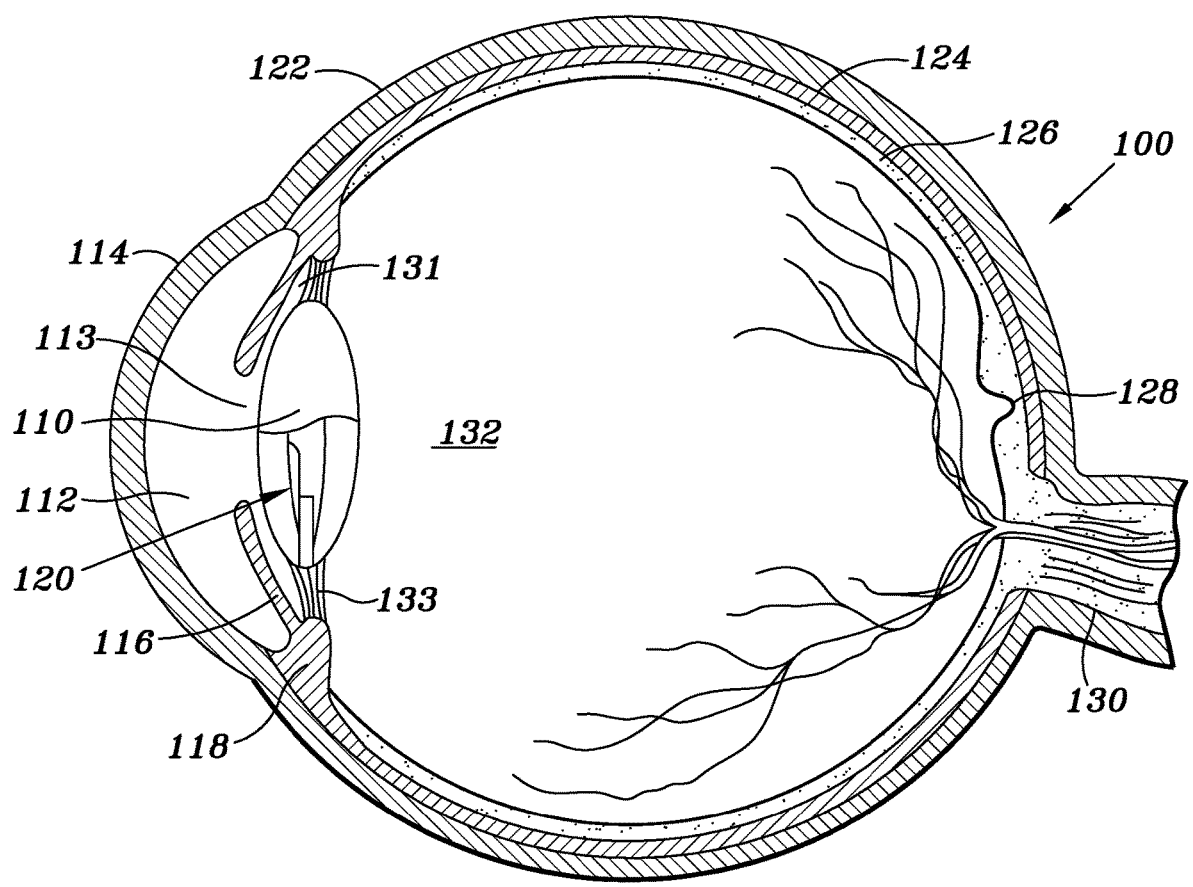

| | | | |
|---|---|---|---|
| 10,299,911 B2* | 5/2019 | Clough | A61F 2/16 |
| 2010/0312336 A1 | 12/2010 | Hong et al. | |
| 2012/0029631 A1 | 2/2012 | Wanders et al. | |

FOREIGN PATENT DOCUMENTS

| | | |
|---|---|---|
| WO | 2010095938 | 8/2010 |
| WO | 2010147455 | 12/2010 |
| WO | 2012118371 | 9/2012 |

OTHER PUBLICATIONS

European Examination Report for Application No. 13185822.7 dated May 10, 2019.
USPTO Issue Notification for U.S. Appl. No. 15/855,658 dated May 8, 2019.
USPTO Notice of Allowance for U.S. Appl. No. 15/855,658 dated Jan. 10, 2019.
USPTO Office Action for U.S. Appl. No. 15/855,658 dated Sep. 5, 2018.
European Search Report for Application No. 13185822.7 dated Jul. 2, 2014.
LENTIS Mplus; by Oculentis, www.oculentis.com; pp. 1-2; Feb. 2012 Edition.
LENTIS Intraocular Lenses; by Oculentis, www.oculentis.com; pp. 1-8; Jun. 2012 Edition.
USPTO Office Action for U.S. Appl. No. 13/671,900 dated Jun. 5, 2014.
USPTO Office Action for U.S. Appl. No. 13/671,900 dated Apr. 11, 2013.
USPTO Final Office Action for U.S. Appl. No. 13/671,900 dated Apr. 8, 2015.
USPTO Final Office Action for U.S. Appl. No. 13/671,900 dated Dec. 4, 2014.
USPTO Final Office Action for U.S. Appl. No. 13/671,900 dated Nov. 25, 2013.
USPTO Notice of Allowance for U.S. Appl. No. 13/671,900 dated Apr. 21, 2016.
USPTO Office Action for U.S. Appl. No. 15/209,313 dated Mar. 21, 2017.
USPTO Final Office Action for U.S. Appl. No. 15/209,313 dated Nov. 16, 2016.
USPTO Notice of Allowance for U.S. Appl. No. 15/209,313 dated Oct. 24, 2017.
USPTO Issue Notification for U.S. Appl. No. 15/209,313 dated Jan. 24, 2018.
USPTO Issue Notification for U.S. Appl. No. 13/671,900 dated Aug. 17, 2016.
European Search Report for Application No. 13185822.7 dated Oct. 5, 2019.

* cited by examiner

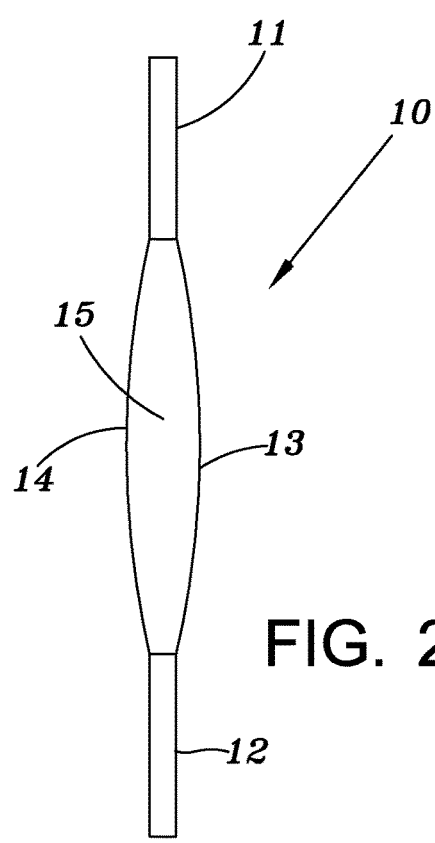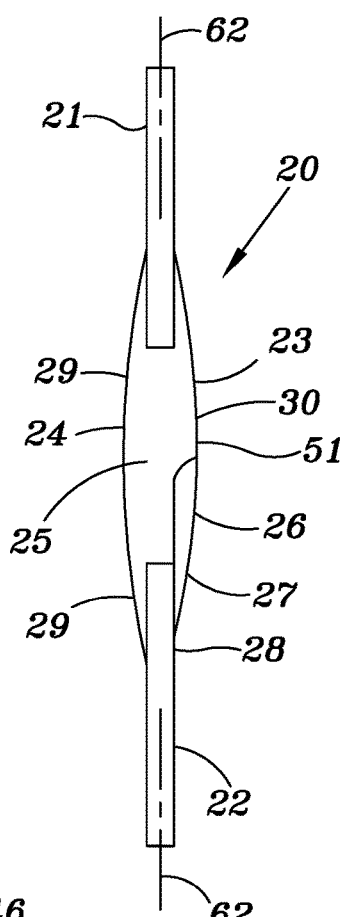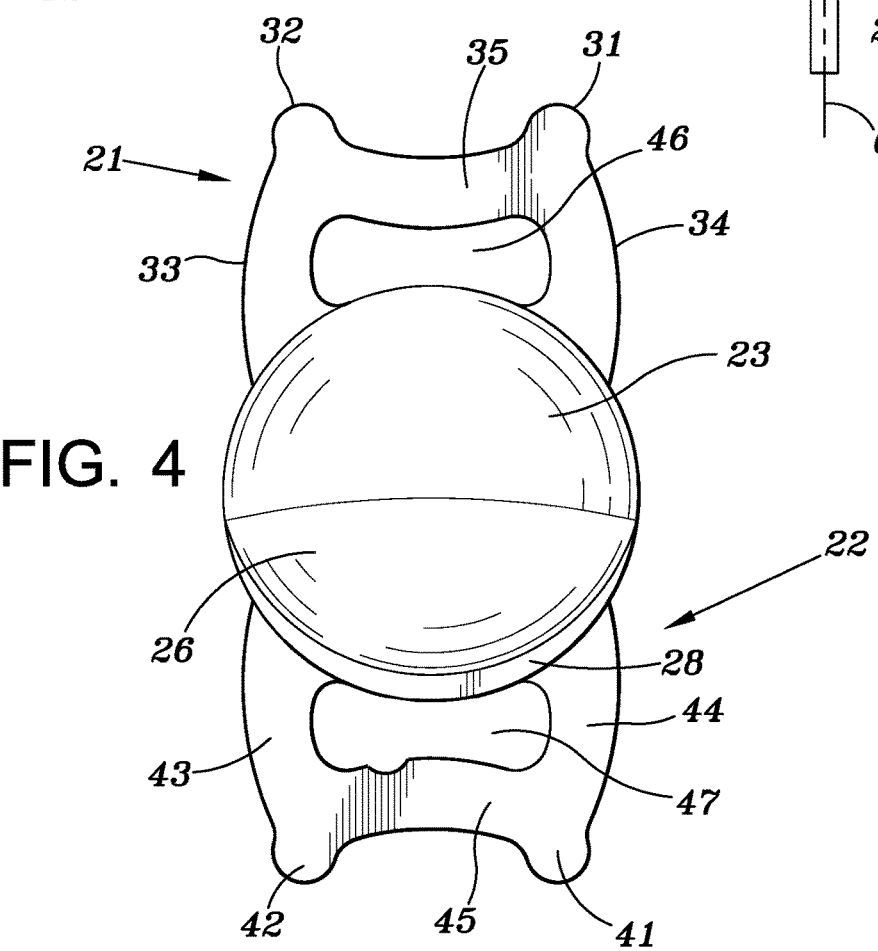

ASPHERICAL MULTIFOCAL INTRAOCULAR LENS

CROSS REFERENCE TO RELATED APPLICATIONS

This application is a continuation of U.S. application Ser. No. 15/855,658 filed Dec. 27, 2017 which is a continuation of application Ser. No. 15/209,313 filed Jul. 13, 2016 which a continuation application of U.S. application Ser. No. 13/671,900 filed Nov. 8, 2012, which are incorporated by reference herein in their entirety.

BACKGROUND OF INVENTION

1. Field of the Invention

The present invention is for an intraocular lens that is typically used as a replacement for the natural lens of the human eye. In the event that the natural lens of the human eye is removed, for example during cataract surgery, an intraocular lens is typically implanted in the lens capsule as a replacement for the natural lens.

2. Description of Related Art

There are several types of intraocular lenses (IOL) that have been developed. They include aspheric lenses, multifocal lenses and accommodating lenses. Also improved haptics for securing the lens within the lens capsule have been developed. These designs to some extent result in aberations and create a halo effect or result in reduced contrast and/or brightness.

BRIEF SUMMARY OF THE INVENTION

The current invention overcomes the drawbacks in the prior art with a unique configuration. The lens of the current invention is formed as an aspheric lens with an added lens surface formed on the posterior portion of the lens. Integral with the lens is a haptic system that securely mounts the lens centrally within the lens capsule and thus minimize any "halo" effect or other aberations.

BRIEF DESCRIPTION OF THE SEVERAL VIEWS OF THE DRAWING(S)

FIG. 1 is a schematic view of the human eye.
FIG. 2 is a side view of a conventional intraocular lens.
FIG. 3 is a side view of an intraocular lens according to an embodiment of the invention.
FIG. 4 is a front view of the lens shown in FIG. 2

DETAILED DESCRIPTION OF THE INVENTION

Referring to FIG. 1 it can be seen that the relevant portions of the eye for purposes of this invention are as follows. Eye 100 has a natural lens capsule 110 in which the natural lens is located and pupil 113, which is surrounded by iris 116. The area forward of the lens capsule 110 is generally referred to as the anterior chamber 112 and the area rearward of the lens capsule 110 is referred to as the posterior chamber 132. The lens capsule 110 is held in place by ciliary zonules 133 which extend between the lens capsule 110 and the ciliary body 118. The space 131 between the iris 116 and the ciliary zonules 133 is referred to as the ciliary sulcus 131. The eye also includes cornea 114, sclera 122, choroaid 124, retina 126, fovea 128 and optic nerve 130.

For cataract surgery, a small incision is normally made at the junction of cornea 114 and sclera 122 and the natural lens can be removed from the lens capsule 110 by phacoemulsification, for example. An intraocular lens (IOL) is then implanted within the lens capsule through the smile initial incision.

FIG. 2 discloses a conventional aspherical lens 10 which includes a central lens portion 15 having opposing convex lens surfaces 14 and 13. Suitable haptics 11 and 12 extend outwardly from the lens portion 15 for securing the lens within the lens capsule.

FIG. 3 illustrates an embodiment of the invention. Intraocular lens 20 has a posterior surface 24 which is aspherical in shape. Posterior radius of surfaces 29 are of equal value. The anterior surface 51 of lens 20 has a first aspherical lens surface 23 which has a radius equal to radius of surfaces 29 and a second lens surface 27 of a smaller radius, thus forming a higher power lens 26 than that of lens surface 23.

The radius of surface 27 is less than that of lens surface 23 so that in forming lens 26, a flat surface 28 will be formed on the outer periphery of the anterior side of the lens as shown in FIGS. 3 and 4. Flat surface 28 lies in a plane that is parallel to the longitudinal axis 62 of the lens.

FIG. 4 illustrates the haptics utilized to secure the lens within the lens capsule. The haptics are formed in the manner disclosed in U.S. Pat. No. 6,261,321, the entire contents of which is hereby incorporated by reference thereto. Upper haptic 21 includes vertical legs 33, 34 and cross member 35 extending between legs 33 and 34. Upper haptic 51 also includes a pair of footplates 31 and 32. Legs 33, 34 and cross member 25 circumvent an opening 46. The footplates are preferably lentricular-shaped.

Lower haptic 22 is formed similar to haptic 51 and includes lower legs 43, 44 and cross member 45 extending between legs 43 and 44. The legs, cross member 45 and lower lens 26 circumvent opening 47. Lower haptic 52 also includes a pair of footplates 41 and 42 of lenticular shape.

Lenses 20 may be formed from a single body of a conventional material utilized for intraocular lens such as acrylic with twenty-six percent water. Lens surface 26 can be formed by using a Fast Tool System available from Ametek Precitech, Inc., located in Keene, New Hampshire. The conic bi-aspheric shape of the lens can be determined according to the methodology described in U.S. Pat. No. 7,350,918, the content of which is hereby expressly incorporated herein by reference thereto.

The distance optic on the multifocal surface is approximately 50 to 70 percent of the optical surface, and the near segment is about 50-30 percent of the optic, with the preferred distribution of optic being about 60 percent distance are 40 percent for near.

Although the present invention has been described with respect to specific details, it is not intended that such details should be regarded as limitations on the scope of the invention, except to the extent that they are included in the accompanying claims.

I claim:
1. A multifocal lens comprising:
a posterior lens surface having a first radius of curvature
an anterior aspheric lens surface, said anterior aspheric lens surface having a first aspheric distance optic portion having a radius of curvature equal to the first radius of curvature of the posterior lens surface and a second near optic portion having a radius of curvature less than that of the first portion thereby forming a second optic surface on the anterior lens surface, the second near optic portion having an outer perimeter, and a flat surface extending outwardly from the entire radially outer perimeter of the anterior lens near optic portion.

2. A multifocal lens as claimed in claim 1 wherein the flat surface lies in a plane which is parallel to a longitudinal axis of the lens.

3. A multifocal lens as claimed in claim 1 wherein the distance optic portion on the anterior surface is about 50% to 70% of the anterior surface of the lens and the near optic portion is about 50% to 30% of the anterior surface of the lens.

4. The multifocal lens of claim 1 wherein the distance optic portion on the anterior surface is about 60% of the anterior surface and the second near optic portion on the anterior surface is about 40% of the anterior surface.

5. The multifocal lens according to claim 1 wherein the posterior lens surface, the anterior aspherical distance optic portion and the second near optic portion of the anterior aspheric surface each consists of a convex lens surface only.

6. A method of improving the eyesight of a human comprising:

a) making an incision in an eye of the human;
b) removing a natural lens of the eye; and
c) implanting an intraocular lens, wherein the intraocular lens comprises:
d) a posterior surface, wherein the posterior surface has a radius of curvature and
e) an anterior aspheric lens surface, said anterior aspheric lens surface having a first aspheric distance optic portion having a radius of curvature equal to the radius of curvature of the posterior surface,
f) a second near optic portion having a radius of curvature less than that of the first aspheric distance optic portion thereby forming a second optic surface on the anterior lens surface,
g) the second near optic portion having an outer perimeter, and
h) a flat surface extending outwardly from the entire outer perimeter of the anterior lens near optic portion.

7. The method of claim 6, wherein the posterior surface is aspherical in shape.

8. The method of claim 6, wherein the intraocular lens is made from an acrylic.

\* \* \* \* \*